United States Patent [19]
Bialer et al.

[11] Patent Number: 5,585,358
[45] Date of Patent: Dec. 17, 1996

[54] DERIVATIVES OF VALPROIC ACID AMIDES AND 2-VALPROENOIC ACID AMIDES, METHOD OF MAKING AND USE THEREOF AS ANTICONVULSANT AGENTS

[75] Inventors: Meir Bialer, Jerusalem; Salim Hadad, Kfar Peki'in; Jacob Herzig, Ra'anana; Jeff Sterling, Jerusalem; David Lerner, Jerusalem; Mitchell Shirvan, Jerusalem, all of Israel

[73] Assignees: Yissum Research Development Corporation of the Hebrew University of Jerusalem; Teva Pharmaceutical Industries Ltd., both of Jerusalem, Israel

[21] Appl. No.: 88,074
[22] Filed: Jul. 6, 1993
[51] Int. Cl.[6] .......................... C07K 5/067; A61K 38/05
[52] U.S. Cl. .......................... 514/19; 564/155; 564/159
[58] Field of Search .................... 564/155, 159; 514/19

[56] References Cited

U.S. PATENT DOCUMENTS 4,639,468   1/1987   Roncucci et al. .

FOREIGN PATENT DOCUMENTS 0046707   3/1982   European Pat. Off. .
0250997   1/1988   European Pat. Off. .
0442012   8/1991   European Pat. Off. .

OTHER PUBLICATIONS

Granneman, Xenobiotica 14 (5)375(1984).
Yu, Mol. & Chem Neuropath 15, 37 (1991).
Chemical Abstracts 101 (17), 143458v, 1984.
*Drugs of the Future* 9(8):587–588 (1984).
*Drugs of the Future* 16(8):775 (1991).
Haj–Yehia, A., et al., *Pharmaceutical Research* 6(8):683–689.
Bialer, M., et al., *Eur. J. Clin. Pharmacol.* 38:289–291 (1990).
Bialer, M., *Clin. Pharmacokinet.* 20(2):114–122 (1991).
Hadad, S., et al., *Journal of Pharmaceutical Sciences* 81(10):1047–1050 (1992).

*Primary Examiner*—Robert Gerstl
*Attorney, Agent, or Firm*—John P. White

[57] ABSTRACT

A compound having the structure:

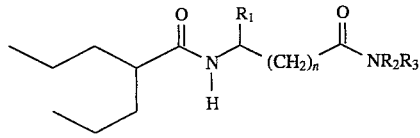

wherein $R_1$, $R_2$, and $R_3$ are independently the same or different and are hydrogen, a $C_1$–$C_6$ alkyl group, an aralkyl group, or an aryl group, and n is an integer which is greater than or equal to 0 and less than or equal to 3. Also provided are a compound containing a 2-valproenoic moiety, pharmaceutical compositions comprising these compounds, and methods of using them for the effective treatment of epilepsy and other neurological disorders.

19 Claims, 2 Drawing Sheets

DERIVATIVES OF VALPROIC ACID AMIDES AND 2-VALPROENOIC ACID AMIDES, METHOD OF MAKING AND USE THEREOF AS ANTICONVULSANT AGENTS

BACKGROUND OF THE INVENTION

The invention relates to new derivatives of 2-propylpentanoic acid (valproic acid, hereinafter VPA), and 2-propyl-2-pentenoic acid, their preparation and use as antiepileptic agents.

VPA and its alkali salts are major drugs in the arsenal of drugs for the treatment of epileptic seizures and convulsions. However, approximately 25% of epileptic patients do not respond to current treatment. Furthermore, VPA itself has considerable adverse effects including hepatotoxicity and teratogenicity. Baille, T. A. and A. W. Rettenmeier, in "Antiepileptic Drugs," ed. by R. H. Levy, F. E. Dreifuss, R. H. Mattson, B. S. Meldrum and J. K. Penry, Raven Press, New York (1989), at 601–619.

One approach to obtain improved antiepileptic agents has been to prepare the primary amide derivatives of VPA and its analogs. M. Bialer, *Clin. Pharmacokinet.* 20:114–122 (1991); M. Bialer, A. Haj-Yehia, N. Barzaghi, F. Pisani, and E. Perucca, *Eur. J. Clin. Pharmacol.*, 289–291 (1990); A. Haj-Yehia and M. Bialer, *J. Pharm. Sci.*, 79: 719–724 (1990). While certain glycinamide derivatives have been disclosed by R. Roncucci, et al., U.S. Pat. No. 4,639,468, issued Jan. 27, 1987, these compounds generally have not been accepted into clinical practice. Thus, an urgent need still exists in the art for developing anti-convulsant agents with improved efficacy and a wider margin between the dose which is therapeutic and that which is neurotoxic.

VPA and 2-ene-VPA-related glycine amides have been disclosed by Granneman, et al., *Xenobiotica*, 14, 375 (1984), to be minor metabolites of VPA. However, an examination of the mass spectral data therein shows that those compounds are in fact VPA and 2-ene-VPA glycine and cannot be glycinamide conjugates, wherein the glycine nitrogen moiety is attached to the VPA or 2-ene-VPA carbonyl. While Granneman, et al., described these compounds as glycine conjugates, they erroneously named them as VPA and 2-ene-VPA glycinamides, rather than valproyl and 2-ene-valproyl glycine; the latter names are in accord with the method of preparation and the mass spectral data reported by Granneman, et al.

SUMMARY OF INVENTION

One object of the present invention is to provide a compound having the structure:

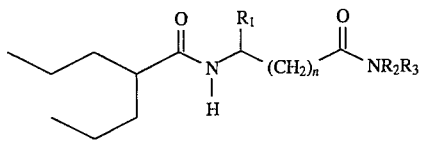
I wherein $R_1$, $R_2$, and $R_3$ are independently the same or different and are hydrogen, a $C_1$–$C_6$ alkyl group, an aralkyl group, or an aryl group, and n is an integer which is greater than or equal to 0 and less than or equal to 3.

Another object of the invention is to provide a compound having the structure:

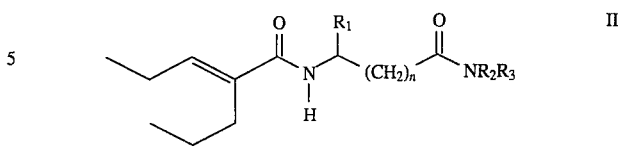
II wherein $R_1$, $R_2$, and $R_3$ are independently the same or different and are hydrogen, a $C_1$–$C_6$ alkyl group, an aralkyl group, or an aryl group, and n is an integer which is greater than or equal to 0 and less than or equal to 3.

BRIEF DESCRIPTION OF THE DRAWINGS

A more complete understanding of the invention and many of its advantages will become apparent by reference to the detailed description which follows when considered in conjunction with the accompanying figures wherein.

DESCRIPTION OF THE INVENTION

Figure 1:
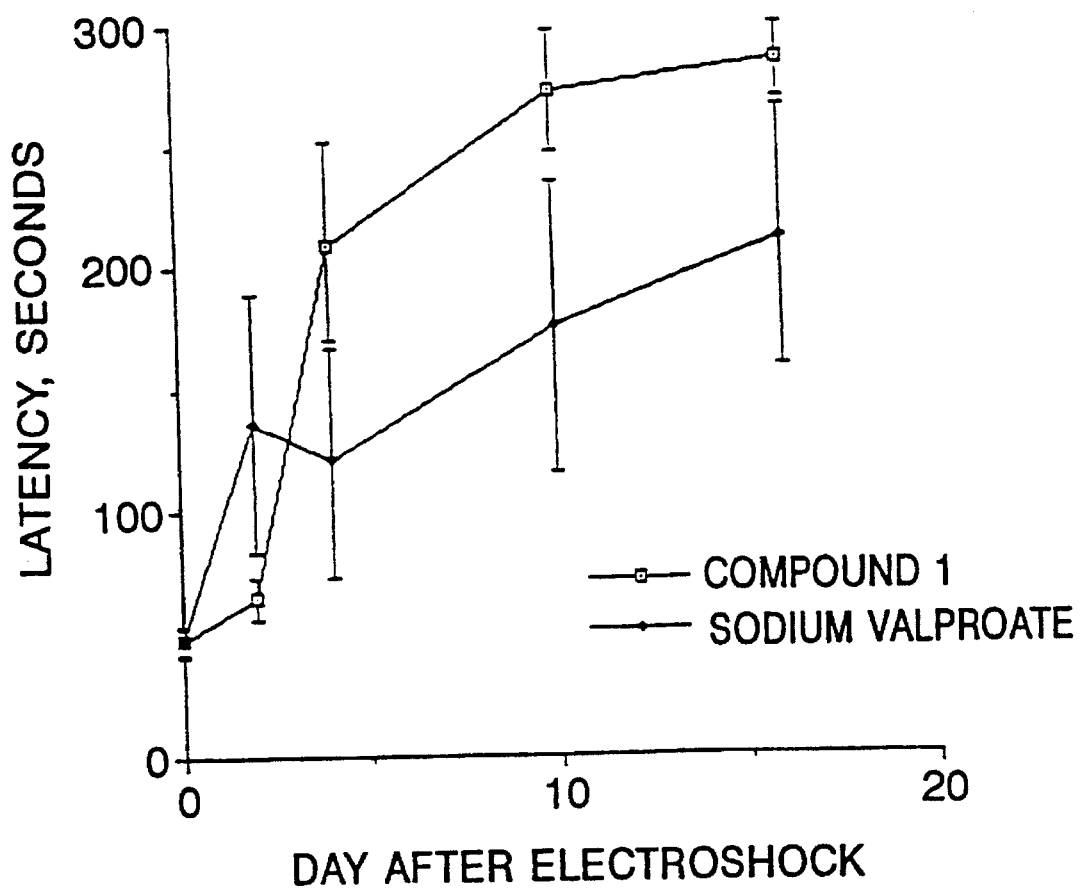
FIG. 1 illustrates performance in the passive avoidance test of rats treated with the indicated drugs for the duration of 28 days at the following daily oral doses: Compound 1, 200 mg/kg; VPA, 500 mg/kg. Tests were performed on day 10 after drug treatment. Latency, in seconds, represents response time to entry into dark compartment. Maximum latency is 300 sec. Longer latencies represent improved performance. Bars represent mean standard error (SEM).

Compounds of particularly high activity and low toxicity result from the coupling of VPA at the carboxyl group with amino acid amides, and have the general structure I. The present invention provides a compound having the structure:

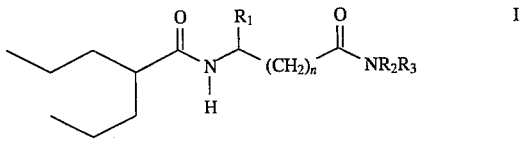
I wherein $R_1$, $R_2$, and $R_3$ are independently the same or different and are hydrogen, a $C_1$–$C_6$ alkyl group, an aralkyl group, or an aryl group, and n is an integer which is greater than or equal to 0 and less than or equal to 3.

In one embodiment, the invention provides the compound of formula I hereinabove shown wherein the $C_1$–$C_6$ alkyl group is a linear chain alkyl group. In another embodiment, the invention provides the compound of formula I hereinabove shown wherein the $C_1$–$C_6$ alkyl group is a branched chain alkyl group. In yet another embodiment, the invention provides the compound of formula I hereinabove shown wherein the aralkyl group is a benzyl, alkylbenzyl, hydroxybenzyl, alkoxycarbonylbenzyl, aryloxycarbonylbenzyl, carboxybenzyl, nitrobenzyl, cyanobenzyl, or halobenzyl group. In still another embodiment, the invention provides the compound of formula I wherein the aryl group is a phenyl, naphthyl, anthracenyl, pyridinyl, indolyl, furanyl, alkylphenyl, hydroxyphenyl, alkoxycarbonylphenyl, aryloxycarbonylphenyl, nitrophenyl, cyanophenyl, halophenyl group, mercaptophenyl, or aminophenyl group.

In preferred embodiments, examples of the compound according to the invention include:

N-(2-n-propylpentanoyl)glycinamide;

N-(2-n-propylpentanoyl)glycine-N'-methylamide;

N-(2-n-propylpentanoyl)glycine-N'-butylamide;

N-(2-n-propylpentanoyl)leucinamide;

N-(2-n-propylpentanoyl)alanine-N'-benzylamide;

N-(2-n-propylpentanoyl)alaninamide;

N-(2-n-propylpentanoyl)-2-phenylglycinamide;

N-(2-n-propylpentanoyl)-4-aminobutyramide;

N-(2-n-propylpentanoyl)-β-alaninamide;

N-(2-n-propylpentanoyl)threoninamide; and

N-(2-n-propylpentanoyl)glycine-N',N'-dimethylamide.

In addition, novel compounds having the general structure II exhibiting high activity and low toxicity are related to those having general structure I, except for having a double bond in the 2-position.

The invention therefore provides a compound having the structure:

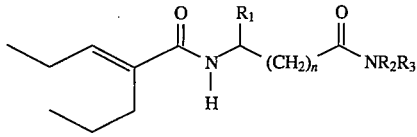

II wherein $R_1$, $R_2$, and $R_3$ are independently the same or different and are hydrogen, a $C_1-C_6$ alkyl group, an aralkyl group, or an aryl group, and n is an integer which is greater than or equal to 0 and less than or equal to 3.

In one embodiment, the invention provides the compound of formula II hereinabove shown wherein the $C_1-C_6$ alkyl group is a linear chain alkyl group. In another embodiment, the invention provides the compound of formula II hereinabove shown wherein the $C_1-C_6$ alkyl group is a branched chain alkyl group. In still another embodiment, the invention provides the compound of formula II hereinabove shown wherein the aralkyl group is a benzyl, alkylbenzyl, hydroxybenzyl, alkoxycarbonylbenzyl, aryloxycarbonylbenzyl, carboxybenzyl, nitrobenzyl, cyanobenzyl, or halobenzyl group. In yet another embodiment, the invention provides the compound of formula II hereinabove shown wherein the aryl group is a phenyl, naphthyl, anthracenyl, pyridinyl, indolyl, furanyl, alkylphenyl, hydroxyphenyl, alkoxycarbonylphenyl, aryloxycarbonylphenyl, nitrophenyl, cyanophenyl, halophenyl group, mercaptophenyl, or aminophenyl group.

In preferred embodiments, examples of the compound of formula I according to the invention include:

N-(2-n-propylpent-2-enoyl)glycinamide;

N-(2-n-propylpent-2-enoyl)alaninamide; and

N-(2-n-propylpent-2-enoyl)glycine-N'-methylamide.

The invention further provides a pharmaceutical composition which comprises any compound hereinabove shown in a therapeutically effective amount and a pharmaceutically acceptable carrier. The invention provides a pharmaceutical composition wherein the therapeutically effective amount is an amount from about 10 to about 500 mg. The invention encompasses a pharmaceutical composition as hereinabove described wherein the carrier is a solid and the composition is a tablet. The invention also encompasses a pharmaceutical composition as hereinabove described wherein the carrier is a gel and the composition is a suppository. The invention further encompasses a pharmaceutical composition as hereinabove described wherein the carrier is a liquid and the composition is a solution.

The invention provides a method of treating a subject afflicted with epilepsy which comprises administering to the subject an amount of the compound according to the invention effective to treat epilepsy in the subject.

The invention also provides a method of treating a subject afflicted with affective illness which comprises administering to the subject an amount of the compound according to the invention effective to treat the affective illness in the subject.

The invention additionally provides a method of treating a subject afflicted with cognitive disorders which comprises administering to the subject an amount of the compound according to the invention effective to treat cognitive disorders in the subject.

The invention further provides a method of treating a subject afflicted with neurodegenerative disease which comprises administering to the subject an amount of the compound according to the invention effective to treat neurodegenerative disease in the subject.

The invention also provides a method of treating a subject afflicted with dyskinesiae which comprises administering to the subject an amount of the compound according to the invention effective to treat dyskinesiae in the subject.

The invention still further provides a method of treating a subject afflicted with neurotoxic injury which comprises administering to the subject an amount of the compound according to the invention effective to treat neurotoxic injury in the subject.

The invention provides a method of alleviating convulsions in a subject afflicted with epilepsy which comprises administering to the subject an amount of the compound according to the invention effective to alleviate convulsions in the subject.

The invention also provides a method of treating a subject afflicted with stroke which comprises administering to the subject an amount of the compound according to the invention effective to treat stroke in the subject.

The invention additionally provides a method of treating a subject afflicted with brain ischemia which comprises administering to the subject an amount of the compound according to the invention effective to treat brain ischemia in the subject.

The invention still further provides a method of treating a subject afflicted with head trauma injury which comprises administering to the subject an amount of the compound according to the invention effective to treat head trauma injury in the subject.

The compounds of general formulas I and II are potent anticonvulsant agents in conventional models of human epilepsy. Several of the compounds have a surprisingly better therapeutic profile than milacemide, VPA, VPA amide analogs or N-valproyl glycine. Furthermore, they may also be useful in the treatment of other CNS dysfunctions.

Suprisingly, the compounds of the invention are highly effective in the MES (maximal electroshock), electrical kindling model, and scMet (subcutaneous pentylenetetrazol) tests. The median effective doses ($ED_{50}$) of the agents claimed herein are considerably lower than those required to produce neurological impairment.

Therefore, results in animal models distinguish the compounds of the present invention from other antiepileptic agents and indicate that some of the disclosed compounds are effective against generalized and partial seizures, in addition to other forms of epilepsy, including absence seizures.

Some of the compounds of this invention possess chiral centers. It is a further embodiment of this invention that these compounds may comprise substantially pure D or L enantiomers or racemic mixtures. It is to be understood that compounds of the general formula II may be of the E-(trans) or Z-(cis) geometric configuration, or a mixture thereof.

The compounds of general formula I are diamides of valproic acid and may be prepared via conventional amidation processes, e.g., by reacting an activated form of the aforementioned acid either with an amino acid amide of the general formula III, where $R_1$, $R_2$, $R_3$ are the same or different and may be a hydrogen, an alkyl group ($C_1$–$C_6$), an aralkyl group or aryl group, and n=0 to 3, or with an amino acid derivative of the general formula IV, in which $R_1$ and n are the same as for III, and $R_4$ is hydrogen or a $C_1$–$C_3$ alkyl group. The resultant valproyl amino acid derivative V (wherein $R_4$ is a lower alkyl group) is reacted with amines of the general formula VII, or first activated (wherein $R_4$ is hydrogen), and the activated form of the acid, VI, is then reacted with VII.

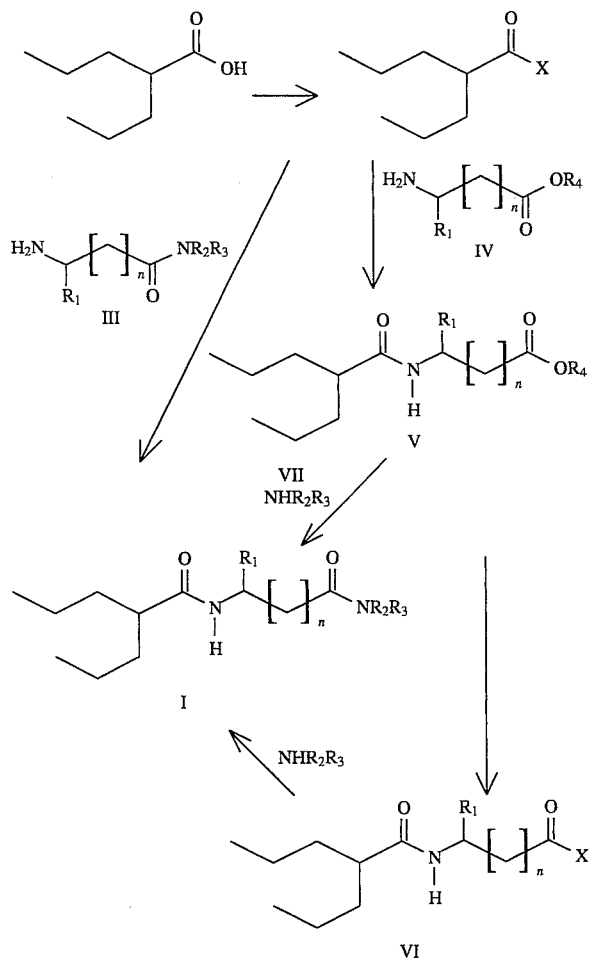

$R_4$ = H or $C_1$–$C_3$ alkyl
X = halide or activated ester, e.g., N-oxysuccinimide Thus, compounds I and V may be prepared in a biphasic system consisting of a basic aqueous solution of amino acid amides III or amino acid esters IV and a solution of valproyl chloride in an inert water-immiscible organic solvent, e.g. dichloromethane or toluene, at a temperature ranging between 0° and 50° C., preferably at 0°–10° C., for a period of 1 to 24 hrs, preferably 1 to 5 hrs.

The basic substance employed for the purpose may be either alkali, such as sodium hydroxide, potassium hydroxide, or potassium carbonate, or an aliphatic or aromatic tertiary amine, preferably triethylamine, and must be present in a quantity sufficient to neutralize the hydrohalic acid formed during the reaction.

Compounds I and V may also be prepared by reacting an activated ester of VPA with amino acid amides III or amino acid ester IV. Thus, VPA is reacted with an activating agent, e.g., N-hydroxysuccinimide, pentafluorophenol, pentachlorophenol, or 1-hydroxybenzotriazole, in the presence of a dehydrating reagent such as a dialkylcarbodiimide, e.g., dicyclohexylcarbodiimide, diisopropylcarbodiimide, or N-(dimethylaminopropyl)-N'-ethylcarbodiimide, at a temperature ranging from 0°–50° C., preferably at 0°–25° C., in an inert solvent, such as tetrahydrofuran, dioxane, 1,2-dimethoxyethane, dichloromethane, or N,N-dimethylformamide. The resulting activated ester may be isolated and purified, or used directly in situ. The activated ester, whether purified or used directly, is reacted with III or IV, under the same conditions leading to condensation as detailed hereinabove.

The reaction of compounds V with amines $R_2R_3NH$ may be carried out in a wide variety of organic solvents, including in an aprotic solvent which is a saturated or aromatic hydrocarbon, such as hexane, benzene, or petroleum ether, or a halogenated solvent, such as chloroform or dichloromethane, in a protic or alcoholic solvent, such as methanol or ethanol, or water. Preferably, the solvent is methanol. The reaction proceeds effectively at a temperature ranging from ambient to reflux, but preferably at 50°–70° C.

Compounds III may be used either as free bases or as their addition salts, formed by treatment of the free bases with an inorganic acid, such as tetrafluoroboric acid, hydrochloric acid, phosphoric acid, or sulfuric acid, or with an organic acid, such p-toluenesulfonic acid, acetic acid, or benzoic acid. Compounds III may be either a pure enantiomeric form, whether of D or L configuration, or a racemic mixture.

The amino acid amides and esters of general formulas III and IV are either commercially available or, alternatively, prepared from appropriate precursors, as detailed in the following examples.

The compounds of general formula II are diamides of valproenoic acid and may be prepared from the latter analogously to the compuonds of the general formula I.

Valproenic acid [(E)-2-ene valproic acid] may be prepared according to procedures known in the art. G. Taillandier, et al., *Arch. Pharm.* (Weinheim), 310, 394 (1977); C. V. Vorhees, et al., *Teratology*, 43, 583 (1991); R. C. Neuman, Jr., and G. D. Holmes, *J. Amer. Chem. Soc.*, 93, 4242 (1971).

In the practice of the invention, the amount of the compound incorporated in the pharmaceutical composition may vary widely. Factors considered when determining the precise amount are well known to those skilled in the art. Examples of such factors include, but are not limited to, the subject being treated, the specific pharmaceutical carrier, and route of administration being employed and the frequency with which the composition is to be administered. A pharmaceutical composition in unit dose form for treatment of the disorders listed hereinabove comprises 10 to 500 mg of the active ingredient.

In a preferred embodiment, the compound is administered in a pharmaceutical composition which comprises the compound and a pharmaceutically acceptable carrier. As used herein, the term "pharmaceutically acceptable carrier" encompasses any of the standard pharmaceutically accepted carriers, such as a phosphate-buffered saline solution, water, emulsions such as an oil/water emulsion or a triglyceride emulsion, various types of wetting agents, tablets, coated tablets, and capsules. An example of an acceptalbe triglyceride emulsion useful in the intravenous and intraperitoneal administration of the compounds is the triglyceride emulsion commercially known as Intralipid®.

Typically, such carriers contain excipients such as starch, milk, sugar, certain types of clay, gelatin, stearic acid, talc, vegetable fats or oils, gums, glycols, or other known excipients. Such carriers may also include flavor and color additives or other ingredients.

In the practice of the invention, the administration of the pharmaceutical composition may be effected by any of the well known methods including, but not limited to, oral, intravenous, intraperitoneal, intramuscular or subcutaneous or topical administration. Topical administration can be effected by any method commonly known to those skilled in the art and include, but are not limited to, incorporation of the pharmaceutical composition into creams, ointments, or transdermal patches.

The following Experimental Details are set forth to aid in an understanding of the invention, and are not intended, and should not be construed, to limit in any way the invention set forth in the claims which follow thereafter.

EXAMPLE 1

N-(2-n-Propylpentanoyl)glycinamide (compound 1).

A solution of valproyl chloride (108 g, 0.66 mole) in $CH_2Cl_2$ (500 ml) was added dropwise to an ice-cooled solution of glycinamide. HCl (72 g, 0.65 mole), and $Et_3N$ (138 g, 1.37 mole) in water (200 ml). Cooling was discontinued and the two-phase mixture was stirred at RT for 3 hrs, cooled to 5°–8° C., and acidified to pH 2 by means of 1N HCl. The solid was collected by filtration, slurried in water (300 ml), filtered, dried and crystallized from EtOAc, affording 75 g (0.375 mole, 50%) of the title compound as a white crystalline solid, mp 127° C.

Anal. calc. for $C_{10}H_{20}N_2O_2$: C, 59.97; H, 10.06 N, 13.99; Found: C, 60.09; H, 10.25; N, 14.00.

$^1H$ NMR δ ($CDCl_3$): 6.72 (br s, 1H, $CONH_2$), 6.65 (br t, 1H, CONH), 5.75 (br s, 1H, $CONH_2$), 3.98 (d, 2H, gly CαH$_2$), 2.18 (m, 1H, Pr$_2$CH), 1.57, 1.40 (m, 4H, $CH_3CH_2$$\underline{CH_2}$), 1.29 (m, 4H, $CH_3\underline{CH_2}CH_2$), 0.89 (t, 6H, $CH_3$) ppm.

MS: 201 ( $MH^+$, 100 ), 184 ($MH^+$–$NH_3$, 24 ).

IR: 3240, 3312, 3181, 2953, 2932, 2872, 1676, 1630, 1549, 431, 1325, 1271, 1221 $cm^{-1}$

EXAMPLE 2

N-(2-n-Propylpentanoyl)leucinamide.

The title compound was prepared from valproyl chloride (2.0 g, 12.3 mmole) and DL-leucinamide hydrochloride (2.0 g, 12.05 mmole), according to the procedure described in Ex. 1. 2.36 g (9.2 mmole, 76%) of a white crystalline solid, mp 151°–2° C., was thus obtained.

Anal. calc. for $C_{14}H_{28}N_2O_2$: C, 65.58; H, 11.01; N, 10.93; Found: C, 65.28; H, 10.89; N, 10.86.

$^1H$ NMR δ (DMSO): 7.85 (br d, 1H, CONH), 7.20 (br s, 1H, $CONH_2$), 6.89 (br s, 1H, $CONH_2$), 4.27 (m, 1H, leu CαH), 2.25 (m, 1H, Pr$_2$CH), 1.60, 1.42, 1.20 (m, 11H, $CH_3$$\underline{CH_2CH_2}$, $Me_2\underline{CHCH_2}$), 0.88 (d, 3H, leu Me), 0.83 (d, 3H, leu Me), 0.83 (br t, 6H, Me) ppm.

MS: 257 (MH+, 100), 240 ($MH^+$–$NH_3$, 32).

IR: 3410, 3300, 2955, 2925, 1720, 1655, 1645, 1540, 1260 $cm^{-1}$.

EXAMPLE 3

N-(2-n-propylpentanoyl)-2-phenylglycinamide.

A solution of valproyl chloride (1.95 g, 12 mmole) in 1,2-dimethoxyethane (DME, 30 ml) was added to an ice-cooled suspension of phenylglycinamide (1.80 g, 12 mmole, prepared from DL-phenylglycinonitrile, Ger. off. 2637204) and Et3N (2.4 g, 24 mmole) in DME (35 ml). The reaction mixture was stirred under a nitrogen atmosphere for 24 hrs at RT, and the resultant product was collected by filtration, washed with cold hexane (50 ml) and taken into EtOAc/H20 (200 ml:175 ml). The organic layer was separated, washed successively with satd. NaHC03, 0.1N HCl and satd. NaCl, dried and evaporated to dryness. The crude product was crystallized from EtOAc, affording 2.50 g (9.06 mmole, 75%) of the title compound as a white crystalline solid, mp 190°–1° C.

Anal. calc. for $C_{16}H_{24}N_2O_2$: C, 69.53; H, 8.75; N, 10.14; Found: C, 68.26; H, 8.57; N, 9.96.

$^1H$ NMR δ (DMSO): 8.36 (br d, 1H, CONH), 7.65 (br s, 1H, CONH), 7.46–7.22 (m, 5H, Ph), 7.10 (br s, 1H, $CONH_2$), 5.46 (d, 1H, Ph—$\underline{CH}$), 2.44 (m, 1H, Pr$_2$CH), 1.40, 1.22, 1.10 (m, 8H, $CH_3\underline{CH_2CH_2}$), 0.85 (t, 3H, Me), 0.78 (t, 3H, Me) ppm.

MS: 277 ($MH^+$, 56), 201 (100).

IR: 3400, 3300, 2950, 2910, 1735, 1685, 1560, 1400 $cm^{-1}$.

EXAMPLE 4

N-(2-n-Propylpentanoyl)alanine methyl ester.

A solution of DL-alanine methyl ester hydrochloride (13.7 g, 98 mmole) and Et$_3$N (20.2 g, 200 mmole) in water (50 ml) was added dropwise to an ice-cooled solution of valproyl chloride (15.0 g, 92 mmole) in $CH_2Cl_2$ (150 ml). After completion of addition the reaction mixture was stirred for 4 hrs. at RT. The layers were then separated and the aqueous layer extracted with $CH_2Cl_2$. The combined organic phases were washed successively with water, satd. $NaHCO_3$, 0.1N HCl and satd. NaCl, dried and evaporated to dryness. The residue was treated with hexane (60 ml), and the resultant solid was collected by filtration, washed with hexane and dried to give 14.2 g (62 mmole, 63%) of the title compound as a white solid, mp 72°–3° C.

$^1H$ NMR δ ($CDCl_3$): 6.02 (br d, 1H, NH), 4.63 (quintet, 1H, ala CαH), 3.75 (s, 3H, OMe), 2.08 (m, 1H, Pr$_2$$\underline{CH}$), 1.6, 1.4, 1.32 (m, 8H, $CH_3\underline{CH_2CH_2}$), 1.40 (d, 3H, ala Me), 0.89 (t, 6H, Me) ppm.

MS: 230 ($MH^+$, 100), 127 (7), 104 (16).

IR: 3300, 2925, 1740, 1630, 1540 $cm^{-1}$.

EXAMPLE 5

N-(2-n-Propylpentanoyl)glycine methyl ester.

The title compound was prepared from valproyl chloride (19.34 g, 119 mmole) and glycine methyl ester hydrochloride (15.0 g, 119 mmole), according to the procedure described in Ex. 4.22 g (102 mmole, 86%) of an off-white solid, mp 68° C., was thus obtained.

$^1H$ NMR δ ($CDCl_3$): 5.97 (br t, 1H, NH), 4.06 (d, 2H, gly $CH_2$), 3.76 (s, 3H, OMe), 2.14 (m, 1H, Pr$_2$CH), 1.60, 1.45–1.25 (m, 8H, $CH_3\underline{CH_2CH_2}$), 0.90 (t, 6H, Me) ppm.

MS: 216 ($MH^+$, 100), 127 (13).

IR: 3300, 2945, 2920, 1765, 1650, 1550, 1220 $cm^{-1}$.

EXAMPLE 6

N-(2-n-Propylpentanoyl)alaninamide.

Aqueous ammonia (25%, 50 ml) was added dropwise to a solution of N-(2-propylpentanoyl)alanine methyl ester (6.87 g, 30 mmole) in methanol (20 ml), and the reaction mixture was stirred under reflux for 4 hrs. The solid which precipitated upon cooling was filtered, washed with cold hexane, dried and crystallized from EtOAc to give 1.90 g (8.92 mmole, 30%) of the title compound as a white crystalline solid, mp 165°–166° C.

Anal calc. for $C_{11}H_{22}N_2O_2$: C, 61.64; H, 10.35; N, 13.08; Found: C, 61.35; H, 10.26; N, 13.32.

$^1$H NMR δ (DMSO): 7.84 (br d, 1H, CONH), 7.21 (br s, 1H, CONH$_2$), 6.92 (br s, 1H, CONH$_2$), 4.25 (quintet, 1H, ala CαH), 2.24 (m, 1H, Pr$_2$—C$\underline{H}$), 1.42, 1.20 (m, 8H, CH$_3$ C$\underline{H_2}$C$\underline{H_2}$), 1.17 (d, 3H, ala Me), 0.833 (t, 3H, Me), 0.827 (t, 3H, Me) ppm.

MS: 214 (M$^+$,1), 170 (M$^+$–CONH$_2$, 100).

IR: 3390, 3295, 1675, 1620 cm$^{-1}$.

EXAMPLE 7

N-(2-n-Propylpentanoyl)alanine-N'-benzylamide.

The title compound was prepared from N-(2-propylpentanoyl) alanine methyl ester (3.67 g, 16 mmole) according to the procedure described in Ex. 6, except that a methanolic solution of benzylamine (1.5 molar excess) was used, and the reaction mixture was stirred under reflux for 24 hours. 1.4 g (4.6 mmole, 29%) of the title compound as a white solid, mp 139° C., was thus obtained.

Anal calc. for $C_{18}H_{28}N_2O_2$: C, 71.01; H, 9.27; N, 9.21; Found: C, 70.88; H, 9.15; N, 9.24.

$^1$H NMR δ (DMSO): 7.25 (m, 6H, PhCH$_2$N$\underline{H}$), 6.40 (br d, 1H, CONH), 4 61 (quintet, 1H, ala CαH), 4.39 (m, 2H, Ph—C$\underline{H_2}$), 2.06 (m, 1H, Pr$_2$C$\underline{H}$) 1.50, 1.25 (m, 8H, CH$_3$ C$\underline{H_2}$C$\underline{H_2}$), 1.34 (d, 3H, ala Me), 0.87 (t, 3H, Me), 0.82 (t, 3H, Me) ppm.

MS: 304 (M$^+$,34), 198 (M$^+$–PhCH$_2$NH, 11), 171 (44).

IR: 3280, 2945, 2925, 1640, 1550, 1445 cm$^{-1}$.

EXAMPLE 8

N-(2-Propylpentanoyl)glycine-N'-methylamide.

The title compound was prepared from N-(2-propylpentanoyl)glycine methyl ester (5.0 g, 23.2 mmole) and 35% aqueous methylamine ( 56.4 mmole), according to the procedure described in Ex. 7. 2.86 g (13.4 mmole, 58%) of a white crystalline solid, mp 146° C., was thus obtained.

Anal. calc. for $C_{11}H_{22}N_2O_2$: C, 61.65; H, 10.35; N, 13.07; Found: C, 61.36; H, 10.14; N, 12.78.

$^1$H NMR δ (DMSO): 7.99 (br t, 1H, CO$\underline{NH}$CH$_2$), 7.69 (m, 1H, CO$\underline{NH}$CH$_3$), 3.62 (d, 2H, gly CH$_2$), 2.58 (d, 3H, NH $\underline{Me}$), 2.22 (m, 1H, Pr$_2$C$\underline{H}$), 1.45, 1.22 (m, 8H, CH$_3$C$\underline{H_2}$ C$\underline{H_2}$), 0.83 (t, 6H, Me) ppm.

MS: 215 (MH$^+$,100), 197 (MH$^+$–H$_2$O, 23), 184 (MH$^+$ –MeNH$_2$, 65), 127 (8).

IR: 3300, 2960, 2920, 2870, 1660, 1630, 1555, 1440, 1420 cm$^{-1}$.

EXAMPLE 9

N-(2-n-Propylpentanoyl)glycine-N'-butylamide.

The title compound was prepared from N-(2-propylpentanoyl)glycine methyl ester (5.0 g, 23.0 mmole) and butylamine (4.1 g, 55.0 mole), according to the procedure described in Ex. 7. 2.2 g (8.5 mmole, 37%), mp 101° C., was thus obtained.

Anal. calc. for $C_{14}H_{28}N_2O_2$: C, 65.58; H, 11.01; N, 10.93; Found: C, 65.87; H, 11.23; N, 11.38.

$^1$H NMR δ (DMSO): 7.99 (br t, 1H, NH), 7.65 (br t, 1H, NH), 3.63 (d, 2H, gly CH$_2$), 3.05 (m, 2H, CH$_3$CH$_2$CH$_2$ C$\underline{H_2}$NH), 2.22 (m, 1H, Pr$_2$C$\underline{H}$), 1.50–1.16 (m, 12H, CH$_3$ C$\underline{H_2}$C$\underline{H_2}$, CH$_3$C$\underline{H_2}$CH$_2$CH$_2$NH), 0.85 (t, 3H, CH$_3$CH$_2$CH$_2$NH), 0.83 (t, 3H, C$\underline{H_3}$CH$_2$CH$_2$ ) ppm.

MS: 257 (MH$^+$, 100), 184 (MH$^+$–C$_4$H$_9$NH$_2$, 19).

IR: 3300, 2940, 1660, 1635, 1555, 1470, 1435, 1300 cm$^{-1}$.

EXAMPLE 10

N-2-n-Propylpentanoyl)glycine-N'-methylamide.

The title compound was prepared from valproyl chloride (404 mg, 2.5 mmole) and 2-amino-N-methylacetamide (220 mg, 2.5 mmole, prepared from glycine methyl ester hydrochloride and methylamine), according to the procedure described in Ex. 1. 318 mg (1.49 mmole, 59%) of a white crystalline solid was thus obtained, identical to the product described in Ex. 8.

EXAMPLE 11

N-(2-n-Propylpentanoyl)-4-aminobutyramide.

To an ice-cooled solution of N-(2-propylpentanoyl)-4-aminobutyroyl chloride (prepared from N-(2-propylpentanoyl)-4-aminobutyric acid and SOC$_{12,\,5.9}$ g, 24.0 mmole) in dioxane (25 ml), was added dropwise conc. NH$_4$OH (34 ml) over 1 hr. The reaction mixture was then stirred at RT for 20 hrs and evaporated to dryness under reduced pressure. The residue was taken up in an H$_2$O (20 ml) and EtOAC (30 ml) mixture, the mixture stirred vigorously for 5 min. The organic phase was separated, evaporated to dryness under reduced pressure, and the residue crystallized from EtOAc to give 1.4 g (6.1 mmole, 26%) of a crystalline solid, mp 138° C.

Anal calc for $C_{12}H_{24}N_2O_2$: C, 63.13; H, 10.60; N, 12.27; Found: C, 63.12; H, 10.69; N, 12.54.

$^1$H NMR δ (DMSO): 7.81 (br t, 1H, NH), 7.26 (br s, 1H, (CH$_2$)3CON$\underline{H_2}$), 6.73 (br s, 1H, (CH$_2$)$_3$CON$\underline{H_2}$), 3.02 (m, 2H, C$\underline{H_2}$CH$_2$CH$_2$CONH$_2$), 2.11 (m, 1H, Pr$_2$CH), 2.03 (t, 2H, C$\underline{H_2}$CONH$_2$), 1.58 (m, 2H, C$\underline{H_2}$CH$_2$CONH$_2$), 1.42 (m, 2H, C$\underline{H_2}$CHCO), 1.19 (m, 6H, C$\underline{H_2}$C$\underline{H_2}$CHCO), 0.84 (t, 6H, Me) ppm.

MS: 229 (MH$_+$, 100), 127 (17).

IR: 3405, 3300, 3190, 2960, 2935, 2880, 1660, 1655, 1635, 1550, 1445 cm$^{-1}$.

EXAMPLE 12

N-[2-n-Propylpent-(E)-2-enoyl]glycinamide.

A cold solution of glycinamide hydrochloride (6.63 g, 60 mmole) in water (18 ml) and Et$_3$N (12.7 g, 126 mmole) were added slowly to a stirred and ice-cooled solution of (E)-2-ene-valproyl chloride in toluene (40 ml). After completion of addition, the biphasic reaction mixture was stirred at ambient temperature for 3 hrs. Work-up and crystallization according to the procedure in Ex. 1 afforded 6.92 g (34.8 mmole, 58%) of the title compound as a white crystalline solid, mp 112° C.

Anal. calcd. for $C_{10}H_{18}N_2O_2$: C, 60.58; H, 9.13; N, 14.13; Found: C, 60.53; H, 8.86; N, 14.04.

$^1$H NMR δ (CDCl$_3$): 6.97 (br s, 1H, CONH$_2$), 6.91 (br t, 1H, NH), 6.29 (t, 1H, vinyl), 6.05 (br s, 1H, CONH$_2$), 2.28 (m, 2H, CH$_3$C$\underline{H_2}$CH=), 2.17 (m, 2H, CH$_3$CH$_2$C$\underline{H_2}$), 1.42 (m, 2H, CH$_3$C$\underline{H_2}$CH$_2$), 1.05 (t, 3H, Me), 0.93 (t, 3H, Me) ppm.

MS: 199 (MH$^+$, 83), 182 (MH$^+$–NH$_3$, 79), 125 (100).

IR: 3341, 3179, 2955, 2872, 1680, 1601, 1535, 1433, 1319 cm$^{-1}$.

EXAMPLE 13

N-[2-n-Propylpent-(E)-2-enoyl]alanine methyl ester.

The title compound was prepared from (E)-2-enevalproyl chloride (10.95 g, 68.1 mmole) and alanine methyl ester hydrochloride (10.14 g, 72.6 mmole) according to the procedure described in Ex. 4. The crude product was crystallized from hexane to give 13.25 g (58.4 mmole, 86%) of a white crystalline solid, mp 25° C.

$^1$H NMR δ (CDCl$_3$): 6.30 (br d, 1H, NH), 6.23 (t, 1H, vinyl) 4.65 (m, 1H, ala CH), 3.76 (s, 3H, OMe), 2.29 (m, 2H, CH$_3$CH$_2$CH=), 2.17 (m, 2H), 1.43 (d, 3H, ala CH$_3$), 1.43 (m, 2H, CH$_3$CH$_2$CH$_2$), 1.04 (t, 3H, Me), 0.92 (t, 3H, Me) ppm.

MS: 228 (MH$^+$, 100), 196 (NH$^+$+–NH$_3$, 100), 168 (30), 125 (76).

EXAMPLE 14

N-[2-n-Propylpent-(E)-2-enoyl]glycine-N'-methylamide.

The title compound was prepared from N-[2-n-propylpent-(E)-2-enoyl]glycine methyl ester (13.5 g, 63.9 mmole), prepared from 2-ene-valproyl chloride and glycine methyl ester hydrochloride as described in Ex. 5, and 35% aqueous methylamine (15 ml, 169.2 mmole), according to the procedure described in Ex. 7. The amide product was purified by column chromatography and crystallized from EtOAc to give 7.8 g (36.8 mmole, 58%) of a white crystalline solid, mp 68°–9° C.

Anal. calcd. for C$_{11}$H$_2$ON$_2$O$_2$: C, 62.23; H, 9.50; N, 13.20; Found: C, 62.42; H, 9.50; N, 13.05.

$^1$H NMR δ (DMSO): 7.94 (br t, 1H, NH) 7.67 (m, 1H, NHCH$_3$), 6.23 (t, 1H, vinyl), 3.65 (d, 2H, gly), 2.58 (d, 3H, NHCH$_3$), 2.21 (m, 2H, CH$_3$CH$_2$CH=), 2.13 ( m, 2H, CH$_3$CH$_2$CH$_2$), 1.32 (m, 2H, CH$_3$CH$_2$CH$_2$), 0.99 (t, 3H, Me), 0.85 (t, 3H, Me) ppm.

MS: 213 (MH$^+$, 73), 195 (37), 182 (MH$^+$–CH$^+$3NH$_2$, 100), 125 (74).

IR: 3300, 2955, 2925, 1660, 1620, 1560, 1540, 1460 cm$^{-1}$.

EXAMPLE 15

N-[2-n-propylpent-(E)-2-enoyl]alaninamide.

The title compound was prepared from N-[2-n-propylpent-(E)-2-enoyl]alanine methyl ester (9.08 g, 40 mmole) and aqueous ammonia (67 ml), in a manner analogous to that described in Ex. 6, giving 5.0 g (59%) of a white crystalline solid, mp 141°–2° C.

Anal. calcd. for C$_{11}$H$_{20}$N$_2$O$_2$: C, 62.23; H, 9.50; N, 13.20; Found: C, 62.48; H, 9.25; N, 13.18.

$^1$H NMR δ (DMSO): 7.63 (d, 1H, NH) 7.25 (br s, 1H, CONH$_2$), 6.96 (br s, 1H, CONH$_2$), 6.18 (t, 1H, vinyl) 4.25 (m, 1H, ala CH), 2.21 (m, 2H, CH$_3$CH$_2$CH$_2$), 1.31 (m, 2H, CH$_3$CH$_2$CH=), 2.11 (m, 2H, CH$_3$CH$_2$CH$_2$), 1.31 (m, 2H, CH$_3$CH$_2$CH$_2$), 1.23 (d, 3H, ala CH$_3$), 0.99 (s, 3H, Me), 0.84 (s, 3H, Me) ppm.

MS: 213 (MH$^+$, 74), 196 (MH$^+$–NH$_3$, 100), 125 (76).

IR: 3725, 3180, 2950, 1700, 1650, 1605, 1530, cm$^{-1}$

EXAMPLE 16

N-(2-n-Propylpentanoyl)-β-alaninamide.

A mixure of N-(2-n-propylpentanoyl)-β-alanine ethyl ester (4.45 g, 18.29 mmole), prepared from valproyl chloride and β-alanine ethyl ester hydrochloride according to the procedure in Ex. 4, dry formamide (2.74 g, 61.27 mmole) and anhydrous THF (9.2 ml) was heated to 100° C., and a freshly prepared solution of sodium methoxide (12.7 mmole) in MeOH (2.93 ml) was added dropwise over 20 min. The mixture was heated at 100° C. for 4 hours and isopropanol (100 ml) was added. The suspension was heated to reflux, filtered, and the filtrate was evaporated to dryness. The residue was dissolved in a refluxing mixture of water and EtOAc. The layers were separated and the aqueous layer was extracted with EtOAc (4×100 ml). The combined organic layers were washed with water, dried, and evaporated to dryness. The crude product (2.5 g) was crystallized from EtOAc to give 2.20 g (10.28 mmole, 56%) of a white solid, mp 167°–8° C.

Anal. calcd. for C$_{11}$H$_{22}$N$_2$O$_2$: C, 61.64; H, 10.35; N, 13.08. Found: C, 61.41; H, 10.16; N, 12.91.

$^1$H NMR δ (DMSO): 7.82 (br t, 1H, CONH), 7.29 (br s, 1H, CONH$_2$), 6.79 (br s, 1H, CONH$_2$), 3.20 (q, 2H, β-ala), 2.21 (t, 2H, α-ala), 2.12 (m, 1H, (Pr)$_2$CH), 1.41, 1.18 (m, 8H, CH$_3$CH$_2$CH$_2$), 0.83 ( t, 6H, Me ) ppm.

MS: 215 (MH$^+$, 100), 197 (MH$^+$–NH$_3$, $_{69}$), 172 (13), 127 (3).

IR: 3389, 3303, 3202, 2957, 2928, 1653, 1634, 1551, 1456, 1439 cm$^{-1}$.

EXAMPLE 17

N-(2-n-Propylpentanoyl)threoninamide.

A solution of valproyl chloride (3.15 g, 19.4 mmole) in anhydrous 1,2-dimethoxyethane (DME, 48 ml) was added slowly to a suspension of threoninamide hydrochloride (3.0 g, 19.4 mmole) and Et$_3$N (3.88 g, 38.8 mmole) in anhydrous DME (60 ml) at 10°–15° C. The reaction mixture was stirred for 24 hours at RT under N$_2$; the solvent was removed under reduced pressure, and the residue was worked up in a manner analogous to that in Ex. 16. The product was crystallized from EtOAc to give 1.0 g (4.1 mmole, 21%) of a white solid, mp 172°–4° C.

Anal. calcd. for C$_{12}$H$_{24}$N$_2$O$_3$: C, 58.99, H, 9.90; N, 11.47; Found: C, 58.12; H, 9.42; N, 11.43.

$^1$H HMR δ (DMSO): 7.58 (d, 1H, CONH), 7.05 (br s, 2H, CONH$_2$), 4.84 (d, 1H, OH), 4.18 (dd, 1H, α-thr), 3.99 (m, 1H, β-thr), 2.35 (m, 1H, Pr$_2$CH), 1.44, 1.22 (m, 8H, CH$_3$CH$_2$CH$_2$), 1.02 (d, 3H, Me-thr), 0.85 (t, 3H, Me), 834 (t, 3H, Me) ppm.

MS: 245 (MH$^+$, 37), 228 (MH$^+$–NH$_3$, 100).

IR: 3405, 3281, 2957, 2930, 2854, 1688, 1665, 1624, 1549 cm$^{-1}$.

EXAMPLE 18

N-(2-n-Propylpentanoyl)glycine-N',N'-dimethylamide.

N-(2-n-Propylpentanoyl)glycine methyl ester (6.0 g, 29.9 mmole) prepared from valproyl chloride and glycine methyl ester hydrochloride according to the procedure in Ex. 4 was dissolved in MeOH (15 ml) and 40% aqueous dimethylamine (11 ml) was added dropwise. The reaction mixture was refluxed for 19 hr and evaporated to dryness. The reaction mixture was treated with hot ethyl acetate, cooled, and filtered. The filtrate was washed consecutively with sat. NaHCO$_3$ and sat. NaCl solution, dried and evaporated to dryness. The solid residue was crystallized from ethyl acetate/hexane to give 1.50 g of a white solid, mp 78°–80° C.

Anal. calcd. for C$_{12}$H$_{24}$N$_2$O$_2$: C, 63.12, H, 10.59; N, 12.27. Found: C, 62.80, H, 10.64; N, 11.93.

$^1$HNMR δ (DMSO): 7.73 (br t, 1H, CONH), 3.79 (d, 2H, gly), 2.84 (s, 3H, Me), 2.72 (s, 3H, Me), 2.16 (m, 1H, (Pr)$_2$CH), 1.34 (m, 2H), 1.12 (m, 6H), 0.74 (t, 6H, Me) ppm.

MS: 229 (MH$^+$, 100 ), 184 (18).

IR: 3314, 2951, 2924, 2872, 1662, 1630, 1522, 1466 cm$^{-1}$.

EXAMPLE 19

Biological Activity of N-(2-Propylpentanoyl)glycinamide.

All compounds provided herein were screened for their ability to protect against chemically and electrically induced convulsions, in at least two different models of epilepsy. The first model, the subcutaneous pentylenetetrazol (s.c. Met) seizure threshold test, is a standard screening procedure to show efficacy for agents against absence seizures. The second model, the maximal electroshock (MES) test, is used to show efficacy for antiepileptic agents against generalized seizures. In these studies, convulsions were inhibited or prevented in mice after intraperitoneal (i.p.) administration and/or in rats after oral (p.o.) administration of the compounds.

N-(2-Propylpentanoyl)glycinamide (hereinafter compound 1) was further tested in two additional models. The third model, electrical kindling of rats, has been known to show efficacy of antiepileptic agents against complex partial seizures that evolve into generalized motor seizures. In these tests, rats were electrically stimulated via corneal electrodes twice daily for approximately 5 days and then once daily for an additional 10 days. Once the seizure criteria, as described by R. J. Racine, et al., *Electroenceph. Clin. Neurophysiol.*, 32: 281–294 (1972), were met, the test substance was administered p.o. to rats, and the rat electrically stimulated, and observed for the presence or absence of a seizure. In addition, compound 1 was also tested in the subcutaneous bicuculline model (s.c. Bic). For detailed procedures of all the above test models, see E. A Swinyard, et al , in "Antiepileptic Drugs," ed. by R. H. Levy, et al., Raven Press, New York, at 85–100 (1989) and Racine, Id.

Compound 1 showed anticonvulsant activity in rodents in all of the above mentioned tests (MES, s.c. Met, s.c. Bic, and electrical kindling models). The ED50 (rat, p.o.) in the MES model was 73 mg/kg (Table 1). This value is seven times lower (more efficacious) than that found for VPA, and approximately twice that found for phenytoin (Table 1; see E.A. Swinyard, et al., id.). Further, in the electrically kindled rat model, compound 1 (administered p.o.) prevented seizures with an $ED_{50}$ of 162 mg/kg (Table 1). The results are therefore indicative of compound 1 having an efficacy against generalized seizures and complex partial seizures which evolve into generalized motor seizures.

In addition, in the s.c. Bic model, compound 1 provided full protection from seizures in mice, at a dose that was approximately that of literature values for the $ED_{50}$ for VPA. Literature values also show that phenytoin, considered the drug of choice for partial and generalized tonic-clonic seizures, is not effective in this model. See B. J. Wilder and R. J. Rangel, in "Antiepileptic Drugs," ed. by R. H. Levy, et al., Raven Press, New York, at 233–239 (1989).

In the s.c. Met model (mice, i.p.), the $ED_{50}$ for compound 1 was 127 mg/kg (Table 1) as compared to the literature value of 146 mg/kg for VPA. These results further indicate efficacy for compound 1 against absence seizures as well.

EXAMPLE 20

Neurotoxicity of Compound 1.

Neurotoxicity of the claimed agents was also assessed in mice (i.p. adminstration) by the rotorod ataxia test and also in some cases in rats (p.o. administration) by the positional sense test and gait and stance test. See E. A. Swinyard, et al., in "Antiepileptic Drugs," ed. by R. H. Levy, et al., Raven Press, New York, at 85–100 (1989). None of the agents provided in the invention showed neurotoxicity in mice at the test dose of 100 mg/kg. Compound 1 had a median neurological toxic dose ($TD_{50}$) in rats of more than 1000 mg/kg. By comparison, the $TD_{50}$ for VPA was 280 mg/kg. In mice, the difference between $TD_{50}$ values between compound 1 and VPA was smaller, but still significantly higher for compound 1 (less neurotoxic) (Table 1). The protective index (PI, PI=$TD_{50}/ED_{50}$) for compound 1 in rats tested in the MES test is more than 23 times greater than that found for VPA (Table 1). These results are shown to indicate that there is a larger therapeutic dose range that can be administered before neurological side effects are usually observed.

The median lethal dose ($LD_{50}$) of compound 1 in mice (i.p. administration) is more than 4,000 mg/kg. This value is in contrast to VPA whose $LD_{50}$ in the same test was 658 mg/kg. The results, therefore, indicate that compound 1 is considerably less toxic than VPA.

EXAMPLE 21

Neurological Activity of Compound 1.

A major neurological side effect observed in patients on treatment with antiepileptic agents is cognitive impairment. Present data further indicate that at the minimum dose required to provide full protection from seizures induced in rats in the MES test, compound 1 results in less cognitive impairment than VPA. Results from the models used are taken as indicators of major constituents of human cognition.

The studies test for the level of motivation, association and short and long-term memory. The specific studies were the effect of compound 1 on the performance of rats in the locomotor test and passive and active response tests. In the cognitive studies below, doses used for compound 1 and VPA were the minimum doses which give full protection against seizures in the MES test (Compound 1=200 mg/kg and VPA=500 mg/kg).

In the locomotor test, motor activity was recorded 8 to 9 days after the beginning of drug treatment. Locomotion scores were recorded in cages (25×26cm) having a grid of infra-red beams at 4 cm intervals. Two categories of movements were recorded: small movements (those originating in stationary activities such as grooming and scratching), and big movements (those resulting in ambulation and recorded as the simultaneous crossing of more than two beams). Since rats are nocturnal animals, recordings were usually made between 18:00 PM–6:00 AM.

The results in the locomotor test (Table 2) show no significant difference in motor activity between the control and compound 1.

To measure passive avoidance responses, tests were performed on days 10, 12, 14, 20, and 26 after initiation of drug treatment. The apparatus consisted of a lit chamber that can be separated from a dark chamber by a sliding door. In the experiment, a rat is placed in a lit chamber for 30 sec, the door is then opened and the rat moves into the dark chamber with latency that is recorded. Upon entry into the dark chamber, the door is shut and a 0.3 mA footshock is delivered for 3 sec. Retention of the experience is determined after 48 hours by repeating the test and recording the latency. The maximum latency was arbitrarily assigned the value of 300 sec. Longer latencies are taken as a measure of improved memory.

Results from this study show that on day 16 of the test, the group receiving compound 1 retained their acquired knowledge to avoid the electric shock as well as the control group (FIG. 1). The VPA-treated rats, however, were apparently affected by treatment, and performed much worse. These results suggest that VPA adversely affected memory, whereas compound 1 did not have this adverse effect.

The conditioned avoidance response (active avoidance test) of rats was determined in a Hugo-Basile automatic conditioning apparatus, which consists of a shuttle box with two separate floor grids. In this apparatus the rats are conditioned to jump from one side of the box to the other side. The conditioning is a 10 sec stimulus consisting of a light and electric buzzer. At the end of this stimulus the rats which do not jump to the other side of the box receive a 20 sec electroshock (50 V, 0.3 mA) from the grid floor. The rats that do jump to the other side of the box do not receive the shock. The session is then repeated with the same rats 7 days later. Experiments were carried out on days 16–17 and 22–23 from the start of drug treatment, and each rat received 60 trials with a 30 sec interval between each trial.

The following parameters were recorded: a) the number of potential shocks successfully avoided; b) the latency response in seconds for avoiding a potential shock; and c) the total number of crossings made throughout the trials. In this test, a better performance is indicated by an increase in the avoidance of an electric shock, a decrease in the latency time to jump to the other side of the cage, and an increase in the number of times the rats crossed to the other side of the cage.

Figure 2:
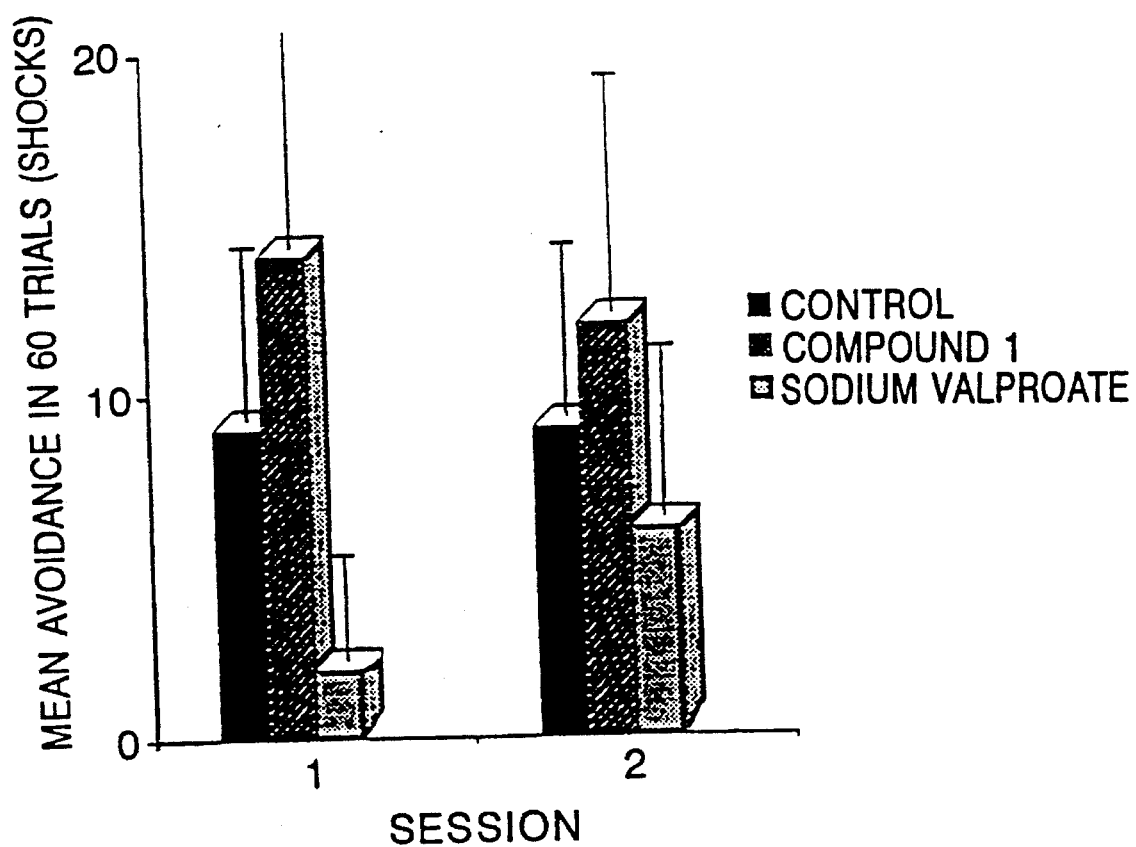
FIG. 2 illustrates performance in the active avoidance test of rats treated with the indicated drugs for the duration of 28 days at the following daily oral doses: Compound 1, 200 mg/kg, VPA, 500 mg/kg. Test was performed on days 16–17 (session 1) and 22–23 (session 2) after initiation of drug treatment. Better performance is indicated by an increase in avoidance score, a decrease in latency time, and an increase in the number of crossings.

Rats treated with compound 1 showed a significantly better performance than the VPA treated group. The performance of the animals treated with compound 1 was similar to that of the control group, whereas the VPA-treated rats had a worse performance (FIG. 2 and Table 3).

The tests stated hereinabove are consistent with the conclusion that compound 1 causes less cognitive impairment than VPA.

Based on the lower $ED_{50}$ and on the higher $TD_{50}$ and $LD_{50}$ values of compound 1, as compared to those of VPA, the former may be considered to act by a unique mechanism, and not as a prodrug of VPA. Moreover, these results are quite unexpected in view of the fact that neither valproylglycine nor milacemide was active when tested in mice (i.p. administration at doses up to 300 mg/kg), in the MES and s.c. Met models.

TABLE 1

Anticonvulsant profile of the claimed and reference antiepileptic agents.

| COMPOUND | COMPOUND 1 (mg/kg) | Phenytoin (mg/kg) | Valproic acid (mg/kg) | Carbamzaepine (mg/kg) |
| --- | --- | --- | --- | --- |
| Rat p.o TD50 MES model | >1000 | >3000 | 281 | 813 |
| ED50 Pi s.c. MET model | 73 >13.7 | 29.8 100 | 490 0.6 | 8.5 95.7 |
| ED50 Pi Electrical kindling model ED50 | — — 162 | N.E. — — | 180 1.6 117 | N.E. — 28.9 |
| Mice i.p. TD50 MES model | 369 | 65.5 | 426 | 71.6 |
| ED50 PI s.c. MET model | 152 2.4 | 9.5 6.9 | 272 1.6 | 8.1 |
| ED50 PI | 127 2.9 | N.E. — | 149 2.9 | N.E. |

The anticonvulsant profile of compound I compared to literature values (for anticonvulsant activity whose experimental protocols were identical to those carried out in the current study) for the prototype anticonvulsant agents VPA and phenytoin. Convulsions were induced in mice and rats by subcutaneous administration of pentylenetetrazol (s.c. Met test) or by electrical stimulation (MES test). N.E. = not effective.

TABLE 2

Activity scores of rats chronically treated with compound 1.

| | Day activity 14.00–20.00 h | | Night activity 20.00–08.00 h | |
| --- | --- | --- | --- | --- |
| Treatment | Big mov. | Total mov. | Big mov. | Total mov. |
| Control (7) | 1939 ± 349 | 6391 ± 983 | 6124 ± 489 | 23750 ± 2075 |
| compound 1 (7) | 2402 ± 307 | 7749 ± 1188 | 7217 ± 765 | 22568 ± 2209 |

TABLE 2-continued

| | Activity scores of rats chronically treated with compound 1. | | | |
|---|---|---|---|---|
| | Day activity 14.00–20.00 h | | Night activity 20.00–08.00 h | |
| Treatment | Big mov. | Total mov. | Big mov. | Total mov. |
| Na Valproate 500 mg/kg (6) | 2784 ± 352 | 8963 ± 1554 | 5832 ± 854 | 18876 ± 2039 |

Activity scores of drug-treated rats, measured in activity cages on days 8–9 after initiation of daily oral dosing with the given drug. Figures are number of crossings ± SEM. Number of rats per group are given in parenthesis.

TABLE 3

| | Active avoidance response of claimed and reference compounds. | | | | |
|---|---|---|---|---|---|
| | Drug treatment | | | | |
| | Session I | | | Session II | | |
| | Avoidance | Latency | Crossings | Avoidance | Latency | Crossings |
| Control (7) | 9 ± 5 | 23 ± 3 | 32 ± 10 | 9 ± 5 | 25 ± 2 | 30 ± 10 |
| compound 1 200 mg/kg (7) | 14 ± 7 | 21 ± 3 | 38 ± 13 | 12 ± 7 | 22 ± 3 | 35 ± 9 |
| Carbamizepine 15 mg/kg (4) | 7 ± 4 | 27 ± 2 | 18 ± 10 | 2 ± 2 | 29 ± 1 | 11 ± 8 |
| Na Valproate 500 mg/kg (6) | 2 ± 3 | 28 ± 0.4 | 13 ± 2 | 6 ± 5 | 27 ± 2 | 16 ± 9 |

Scores in the active avoidance test (conditioned avoidance response) of rats treated with compound 1 and related drugs. The tests in the first session were performed on days 16–17 from initiation of drug administration. Those in session II were performed on days 22–23, that is 7 days following session I. Number of rats in a group are given in parenthesis.

What is claimed is:

1. A compound having the structure:

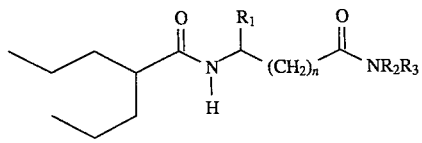

wherein $R_1$, $R_2$, and $R_3$ are independently the same or different and are hydrogen, a $C_1$–$C_6$ alkyl group, an aralkyl group, or an aryl group, and n is equal to 0.

2. The compound of claim 1, wherein the $C_1$–$C_6$ alkyl group is a linear chain alkyl group.

3. The compound of claim 1, wherein the $C_1$–$C_6$ alkyl group is a branched chain alkyl group.

4. The compound of claim 1, wherein the aralkyl group is a benzyl, alkylbenzyl, hydroxybenzyl, alkoxycarbonylbenzyl, aryloxycarbonylbenzyl, carboxybenzyl, nitrobenzyl, cyanobenzyl, or halobenzyl group.

5. The compound of claim 1, wherein the aryl group is a phenyl, naphthyl, anthracenyl, pyridinyl, indolyl, furanyl, alkylphenyl, hydroxyphenyl, alkoxycarbonylphenyl, aryloxycarbonylphenyl, nitrophenyl, cyanophenyl, halophenyl group, mercaptophenyl, or aminophenyl group.

6. A compound of claim 1 selected from the group consisting of:

N-(2-n-propylpentanoyl)glycinamide;

N-(2-n-propylpentanoyl)glycine-N'-methylamide;

N-(2-n-propylpentanoyl)glycine-N'-butylamide;

N-(2-n-propylpentanoyl)leucinamide;

N-(2-n-propylpentanoyl)alanine-N'-benzylamide;

N-(2-n-propylpentanoyl)alapinamide;

N-(2-n-propylpentanoyl)-2-phenylglycinamide;

N-(2-n-propylpentanoyl)threoninamide; and

N-(2-n-propylpentanoyl)glycine-N',N'-dimethylamide.

7. A compound having the structure:

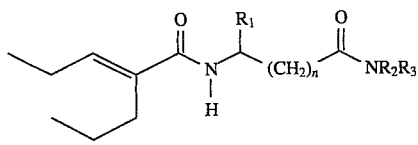

wherein $R_1$, $R_2$, and $R_3$ are independently the same or different and are hydrogen, a $C_1$–$C_6$ alkyl group, an aralkyl group, or an aryl group, and n is an integer which is greater than or equal to 0 and less than or equal to 3.

8. The compound of claim 7, wherein the $C_1$–$C_6$ alkyl group is a linear chain alkyl group.

9. The compound of claim 7, wherein the $C_1$–$C_6$ alkyl group is a branched chain alkyl group.

10. The compound of claim 7, wherein the aralkyl group is a benzyl, alkylbenzyl, hydroxybenzyl, alkoxycarbonylbenzyl, aryloxycarbonylbenzyl, carboxybenzyl, nitrobenzyl, cyanobenzyl, or halobenzyl group.

11. The compound of claim 7, wherein the aryl group is a phenyl, naphthyl, anthracenyl, pyridinyl, indolyl, furanyl, alkylphenyl, hydroxyphenyl, alkoxycarbonylphenyl, aryloxycarbonylphenyl, nitrophenyl, cyanophenyl, halophenyl group, mercaptophenyl, or aminophenyl group.

12. A compound of claim 7 selected from the group consisting of:

N-(2-n-propylpent-2-enoyl)glycinamide;

N-(2-n-propylpent-2-enoyl)alaninamide; and

N-(2-n-propylpent-2-enoyl)glycine-N'-methylamide.

13. A pharmaceutical composition which comprises the compound of claims 1 or 7 or a in a therapeutically effective amount and a pharmaceutically acceptable carrier.

14. The pharmaceutical composition of claim 13 wherein the therapeutically effective amount is an amount from about 10 to about 500 mg.

15. The pharmaceutical composition of claim 14, wherein the carrier is a solid and the composition is a tablet.

16. The pharmaceutical composition of claim 14, wherein the carrier is a gel and the composition is a suppository.

17. The pharmaceutical composition of claim 14, wherein the carrier is a liquid and the composition is a solution.

18. A method of treating a subject afflicted with epilepsy which comprises administering to the subject an amount of the compound of claim 7 effective to treat epilepsy in the subject.

19. A method of treating a subject afflicted with epilepsy which comprises administering to the subject an amount of the compound of claim 1 effective to treat epilepsy in the subject.

* * * * *